(12) United States Patent
Bender et al.

(10) Patent No.: US 9,943,620 B2
(45) Date of Patent: Apr. 17, 2018

(54) CHLORINE DIOXIDE DECONTAMINATION SYSTEM AND METHODS

(71) Applicant: Controlled Performance with Gases, LLC, Louisville, KY (US)

(72) Inventors: Lawrence F. Bender, Lousiville, KY (US); James F. Knoer, Taylorsville, KY (US)

(73) Assignee: Controlled Performance with Gases, LLC, Louisville, KY (US)

( * ) Notice: Subject to any disclaimer, the term of this patent is extended or adjusted under 35 U.S.C. 154(b) by 0 days.

(21) Appl. No.: 14/837,017

(22) Filed: Aug. 27, 2015

(65) Prior Publication Data

US 2016/0058901 A1 Mar. 3, 2016

Related U.S. Application Data

(60) Provisional application No. 62/042,398, filed on Aug. 27, 2014.

(51) Int. Cl.
| | | |
|---|---|---|
| *C01B 6/00* | (2006.01) | |
| *A61L 9/12* | (2006.01) | |
| *A61L 2/20* | (2006.01) | |
| *C01B 11/02* | (2006.01) | |

(52) U.S. Cl.
CPC .............. *A61L 2/20* (2013.01); *C01B 11/024* (2013.01)

(58) Field of Classification Search
CPC ................................ A61L 2/20; C01B 11/024
See application file for complete search history.

(56) References Cited

U.S. PATENT DOCUMENTS

| | | | |
|---|---|---|---|
| 5,597,645 A | 1/1997 | Pike et al. | |
| 6,607,696 B1* | 8/2003 | Hamilton | A61L 2/20 134/6 |
| 8,524,167 B2 | 9/2013 | Regits et al. | |
| 2003/0133834 A1 | 7/2003 | Karle | |
| 2004/0022673 A1* | 2/2004 | Protic | A61L 2/20 422/28 |
| 2004/0211731 A1 | 10/2004 | Ferguson et al. | |
| 2006/0110280 A1* | 5/2006 | Nelson | A23B 7/152 422/3 |
| 2008/0025870 A1* | 1/2008 | Groenewegen | A61L 2/202 422/37 |

(Continued)

OTHER PUBLICATIONS

International Search Report and Written Opinion for PCT Application No. PCT/US2015/47091 dated Jul. 12, 2016.

*Primary Examiner* — Kevin Joyner
(74) *Attorney, Agent, or Firm* — Neustel Law Offices (57) ABSTRACT

A scalable, portable and modular chlorine dioxide fumigant decontamination system having an activating area and a neutralizing area which may be housed separately or as a single operationally connected unit, and which may be configured as a closed loop system connected to a decontamination chamber for decontamination of articles, or as an open loop system for decontamination of interiors and large confined spaces, and employing a specialized activating cup that is permeable to air yet substantially impermeable to water and chlorine dioxide reaction by-products such that directing air through the activation cup releases nearly pure chlorine dioxide fumigant. Methods and articles relating to the system are also described.

28 Claims, 7 Drawing Sheets

(56) References Cited

U.S. PATENT DOCUMENTS

| | | | |
|---|---|---|---|
| 2010/0266448 A1* | 10/2010 | Regits | A61L 2/20 |
| | | | 422/29 |
| 2012/0164025 A1* | 6/2012 | Stockley, III | A61L 2/26 |
| | | | 422/29 |
| 2013/0101477 A1 | 4/2013 | Both et al. | |
| 2013/0216437 A1* | 8/2013 | Sperry | C01B 11/024 |
| | | | 422/112 |
| 2016/0206767 A1* | 7/2016 | Park | A61L 2/10 |

\* cited by examiner

CHLORINE DIOXIDE DECONTAMINATION SYSTEM AND METHODS

PRIORITY

This application claims priority under 35 U.S.C. § 119(3) to U.S. Provisional No. 62/042,398, filed Aug. 27, 2015, the entire disclosure of which is incorporated herein by this reference.

TECHNICAL FIELD

The subject matter of this application relates generally to the chemical decontamination arts and more specifically to chlorine-dioxide fumigant based decontamination systems and methods.

BACKGROUND

Chlorine dioxide (CD or $ClO_2$) was discovered in the early 1800's, and has been approved for a wide variety of commercial disinfecting/sterilizing applications by the EPA, FDA and USDA. Due to its demonstrated efficacy with respect to a wide variety of contaminated surfaces, $ClO_2$ has been called the ideal biocide and the ability of chlorine dioxide to reduce or eliminate microbes, e.g., bacteria, viruses, fungi, mold spores, algae and protozoa, at relatively low concentrations is well-documented. Because $ClO_2$ inactivates microorganisms by oxidizing critical components of a microorganism's membrane proteins, tolerance to $ClO_2$ does not develop, making it an ideal disinfectant/sterilant for repeated-use applications such as in a hospital environment.

$ClO_2$ is a green-yellowish gas with a chlorine-like odor; however $ClO_2$ is a neutral chlorine compound. $ClO_2$ is a small, volatile and very strong molecule. In diluted, watery solutions $ClO_2$ is a free radical. At high concentrations it reacts strongly with reducing agents. Chlorine dioxide is an unstable gas that dissociates into chlorine gas and oxygen gas readily. Further, $ClO_2$ may be photo-oxidized by sunlight and therefore decontamination applications generally proceed in the absence of light. The end-products of $ClO_2$ neutralization/degradation reactions are chloride (Cl—), chlorite (ClO—) and chlorate (ClO3–).

$ClO_2$ is not as reactive as ozone or chlorine and it generally reacts only with sulphuric substances, amines and some other reactive organic substances. In comparison to chlorine and ozone, less chlorine dioxide is required to obtain an active residual disinfectant. It can also be used when a large amount of organic matter is present in the environment.

A significant drawback of $ClO_2$ is that it is explosive under pressure, thus making it difficult to transport. It cannot be transported in liquid phase or under pressure; hence it is typically manufactured on site (in situ). $ClO_2$ is usually produced as a watery solution or gas. It is produced in acidic solutions of sodium chlorite ($NaClO_2$), or sodium chlorate ($NaClO_3$). Sodium chlorite, chlorine gas ($Cl_2$), sodium hydrogen chlorite ($NaHClO_2$) and sulphuric or hydrogen acid are typically used for the production of chlorine dioxide on site. In the presence of sunlight, $ClO_2$ in air will decompose to chlorine and oxygen. The chlorine will react with any moisture in the air to form a hydrochloric acid mist. If the concentration of $ClO_2$ in air in a confined space is above 10%, the chlorine dioxide is at an explosive concentration and can be ignited by almost any form of energy such as sunlight, heat or sparks, including for example, static electrical energy. Concentrations above 40% will generate a decomposition/shock wave if set off by any ignition source.

Other decontamination systems which exploit the beneficial properties of $ClO_2$ fumigant are known in the art. However, these systems generally suffer from production of excess humidity with the fumigant, resulting in production of hydrochloric acid mist and potential to corrode electronic equipment, making the system inconvenient for large-scale building decontamination, since removal of corrosion-sensitive articles must be effectuated prior to decontamination. Further, even when corrosion-sensitive articles are removed from the area, metallic structural components of buildings may be affected. In addition to the corrosive effects of moisture, salts existing as by-products of $ClO_2$ generation reactions and often present in the fumigant, are known to cause damage to structures and articles undergoing decontamination. This is particular problematic to areas that must be repeatedly disinfected, such as in the medical/hospital context, since the damaging effects accrue.

U.S. Pat. No. 8,524,167 (the '167 patent) discloses a $ClO_2$ decontamination system, however it suffers from failure to provide mechanisms for removal of byproducts and relies on humidification as a necessary aspect of effective $ClO_2$ fumigant decontamination, going so far as to add a humidifier to a decontamination chamber. The '167 patent system is unsuitable for corrosion-sensitive articles and environments. A critical consideration is that that the registered concentration of $ClO_2$ cannot be trusted, since chlorine gas is known to influence the sensors toward detection of chlorine dioxide and to result in artificially high concentration read-outs. Chlorine gas is produced as a result of the humidification. Further, the '167 fumigant scrubber relies heavily on carbon, which is rendered less effective by the presence of water. Notably, the use of carbon filtration with non-degraded $ClO_2$ can create an explosive potential because $ClO_2$ can build up in the carbon pores in problematic concentrations. Hence, the use of carbon as a primary neutralizer/scrubber presents a significant fire and safety hazard.

Known $ClO_2$ fumigant systems generally utilize a reaction sachet (bag) for generation of the gas with water, and sparging of the gas product from the liquid. The result is that acid vapor and chlorine gas are often present in the CD fumigant. As noted, both of these gases are highly corrosive to metals, and chlorine, in particular, is incompatible with many non-metallic substances as well. Neutralization of the fumigant is complicated by the presence of these additional toxic gases. Prolonged treatment time results where multiple passes are required for neutralization.

In a highly publicized recent decontamination effort by the U.S. government, a $ClO_2$ fumigant system was employed to decontaminate a building contaminated with Anthrax spores that were released from a letter opened in a mail room. The building was tented prior to fumigation and sparged $ClO_2$ gas was pumped into the building's heating, ventilating and air conditioning (HVAC) system to achieve a target concentration of 500 ppm at 75° F. and 75% relative humidity for 18 hours. Biological indicators (BI) comprising standard *b. subtilus* spore strips were placed throughout the facility. (Standard BIs contain 106 natural pathogens—sufficient to indicate a maximum 6-log spore reduction, however the BI's were not normed to Anthrax). Hence the effectiveness of decontamination was also tested via swipe sampling. Reportedly, the original plan to neutralize the $ClO_2$ with ascorbic acid was abandoned when very high concentrations of chlorine gas were found localized throughout the building. Because the presence of chlorine molecules interferes with ClO$_2$ monitoring to yield false high concentration readings, it was presumed therefore that concentration targets were not actually met and the procedure had to be repeated three times over 9 months for a total cost of nearly 50 million dollars to U.S. taxpayers.

Clearly there remains a need in the art for safe and effective ClO$_2$ fumigant decontamination systems that minimize use of water, minimize agitation/degradation of the CD fumigant, and that avoid dispersal of water vapor, acid and chlorine gas along with the fumigant.

SUMMARY

Accordingly, the present investigators have developed a ClO$_2$ fumigant decontamination system that overcomes these and other deficiencies in the art. In particular, the disclosed system provides a ClO$_2$ fumigant that is substantially free of water vapor, acid vapors and other by-products of ClO$_2$ gas production. Thus, the ClO$_2$ decontamination system may be utilized in a broad range of applications, including for example, sterilization of corrosion-sensitive electronic equipment and metallic substrates, sterilization of environments for human habitation, and sterilization of operating rooms, medical devices, and other environments/devices that may be subject to repeated sterilization. Further, the ClO$_2$ fumigant decontamination system provides an aspect of one-pass neutralization, simplifying and decreasing the expense and time associated with large-scale decontamination projects generally. The system is modular and portable, offering not only increased convenience, but the operational capacity to locate additional ClO2 fumigant activating areas throughout a large area to be decontaminated dependent on target concentrations and area to be decontaminated.

One embodiment of the invention provides decontamination systems comprising: a chlorine dioxide (ClO$_2$) fumigant activating area, optionally, a by-pass flow area, a neutralizing area; a first air blower, preferably having variable speed and in direct fluid communication with the ClO$_2$ fumigant activating area, the by-pass flow area and the neutralizing area; and a valve system for dedicating air flow from the blower to one or more of the areas. The activating area comprises a novel activation cup configured to receive reagents for the in situ generation of ClO$_2$ fumigant. The activation cup is fabricated to be permeable to air and substantially impermeable to water and reaction by-products. The activation cup may be attached to a plate and suspended in the activation area such that air flowing from the first variable speed air blower into the activation area flows through and around the activation cup such that generated ClO$_2$ fumigant passes out of the activation cup with the air flow, while water and reaction by-products remain in the activation cup. Thus, ClO$_2$ fumigant produced according to the inventive decontamination system is substantially free of water vapor, acid vapor and chlorine gas.

Other embodiments provide methods for generating chlorine dioxide fumigant in a directed flow with a minimum of water. The methods comprise (a) providing an activation cup comprising: an outer layer of crush-resistant thermally bondable non-woven fibers molded into a transversely bisected aerodynamically-shaped shell, said shell open at the top and having an interior surface and an exterior surface, said exterior surface and interior surface comprising a pattern of corrugations; at least one filter layer including one filter layer adjacent and adherent to an inner surface of the outer layer, wherein at least one filter layer comprises high-loft electret charged fluorine-coated polyolefin microfibers, wherein the activation cup is adapted to retain water and reaction by-products while permitting gas to pass through; (b) flexibly suspending the activation cup; (c) adding dry reagents for production of ClO$_2$ fumigant to the cup; (d) directing an air flow toward the cup at a low speed such that the corrugations create turbulence resulting in vibration of the cup and acceleration of ClO$_2$ generation, "low" being defined as insufficient to degrade ClO$_2$; (e) adding water to the cup; thereby initiating generation of ClO$_2$ fumigant that is directed out of the cup with the air flow while water and ClO$_2$ generation reaction by-products are substantially retained in the cup.

Further embodiments provide methods for neutralizing chlorine dioxide (ClO$_2$) fumigant in a sealed neutralizing area, said neutralizing area comprising a leak abatement space and a neutralizing space, said neutralizing space comprising a series of treatment stations and at least one blower, the method comprising: (a) blowing ClO$_2$ fumigant to-be-neutralized into a treatment station comprising ultraviolet light, resulting in partially neutralized air, said blowing effectuated at a speed high enough to degrade ClO$_2$; (b) blowing the partially neutralized air from the UV treatment station through a diffusion plate and into a treatment station comprising a neutralizing solution reservoir, thereby creating bubbling and frothing in the reservoir and resulting in substantially neutralized air; (c) capturing and returning solution to the reservoir with a treatment station comprising a humidification filter that permits the substantially neutralized air to pass through the filter and into a treatment area comprising coated zeolite; (d) passing the substantially neutralized air through the coated zeolite to neutralize any remaining ClO$_2$ and other toxic gaseous by-products remaining, resulting in neutralized air; and, (e) optionally, passing the neutralized air through activated carbon to remove odiferous molecules which may be present in the neutralized air.

Embodiments directed to a fumigant activation cup are also disclosed. The cup comprises (a) an outer layer of crush-resistant thermally bondable non-woven fiber molded into a transversely bisected aerodynamically-shaped shell, said shell open at the top and having an interior surface and exterior surface; (b) at least one filter layer, including one filter layer adherent and adjacent to an inner surface of the outer molded layer; (c) an inner layer of crush-resistant fibrous material adjacent and adherent to the at least one filter layer; wherein the at least one filter layer comprises high-loft electrically charged fluorinated polyolefin microfibers and exhibits a higher melting point that the molded layers.

These and additional embodiments and aspects of the invention will be clarified by reference to the accompanying figures and detailed description, below.

BRIEF DESCRIPTION OF THE FIGURES

FIG. 2 A. shows an illustrative cup with a saddle-shaped horizontal cross-sectional shape.

FIG. 5 A. Illustrates a top view of a hospital operating room undergoing decontamination utilizing a main HVAC system and having a temporary wall installed around the operation room, showing a fumigant air flow into a high-efficiency particulate arrestance (HEPA) filter/diffuser positioned centrally over the operating table and into slotted diffusers placed at either side of the operating area in order to create an air curtain around the operating area.

DETAILED DESCRIPTION

When describing embodiments of the system of the invention, the term decontamination may be used to refer to all levels of sanitizing, sterilizing, disinfecting and deodorizing. Decontamination is a term used broadly to describe a process or treatment that renders a medical device, instrument, surface, content, or environmental surface safe for humans. Decontamination includes sterilization and disinfection. Disinfection eliminates virtually all pathogenic non-spore-forming microorganisms but not necessarily all microbial forms on inanimate objects (work surfaces, equipment, etc.). Effectiveness is influenced by the kinds and numbers of organisms, the amount of organic matter, the object to be disinfected and chemical exposure time, temperature and concentration. The CDC recognizes three levels of disinfection: (1) High-level Disinfection: A procedure that kills all organisms with the exception of bacterial spores and certain species, such as the Creutzfeldt-Jakob prion. Most high-level disinfectants can produce sterilization with sufficient contact time. (2) Intermediate-level Disinfection: A procedure that kills vegetative bacteria, including acid-fast *Mycobacterium tuberculosis*, most fungi, and viruses but not bacterial spores. (3) Low-level Disinfection: A procedure that kills most vegetative bacteria (but not *M tuberculosis*), some fungi, and viruses but no spores. Sterilization is destruction all microbial life, including highly resistant bacterial endospores.

The novel $ClO_2$ decontamination system as described herein generates $ClO_2$ in a specialized activation area contained in a sealed portable cabinet using directed air flow to provide target residential concentrations of $ClO_2$ to any desired area for the purpose of decontamination, disinfecting, sterilization, and deodorization. The system components operate in synchrony to achieve safe and highly efficient production of substantially pure $ClO_2$ fumigant. "Substantially pure" $ClO_2$ as used herein is defined as a gas that is between 90 and 99.9% $ClO_2$ by weight, or between 95 and 99.9% $ClO_2$ by weight, or between 98 and 99.5% $ClO_2$ by weight, or over 99% $ClO_2$ by weight. The system is versatile in that it can be configured and scaled for small, large and complex configurations and environmental applications. Components of the system may be separated and used independently or in multiples, depending on the decontamination environment and needs.

Embodiments and aspects of the invention will be described with reference to the Figures, which are intended to be illustrative and not limiting of the scope of the invention as defined by the claims.

Figure 1:
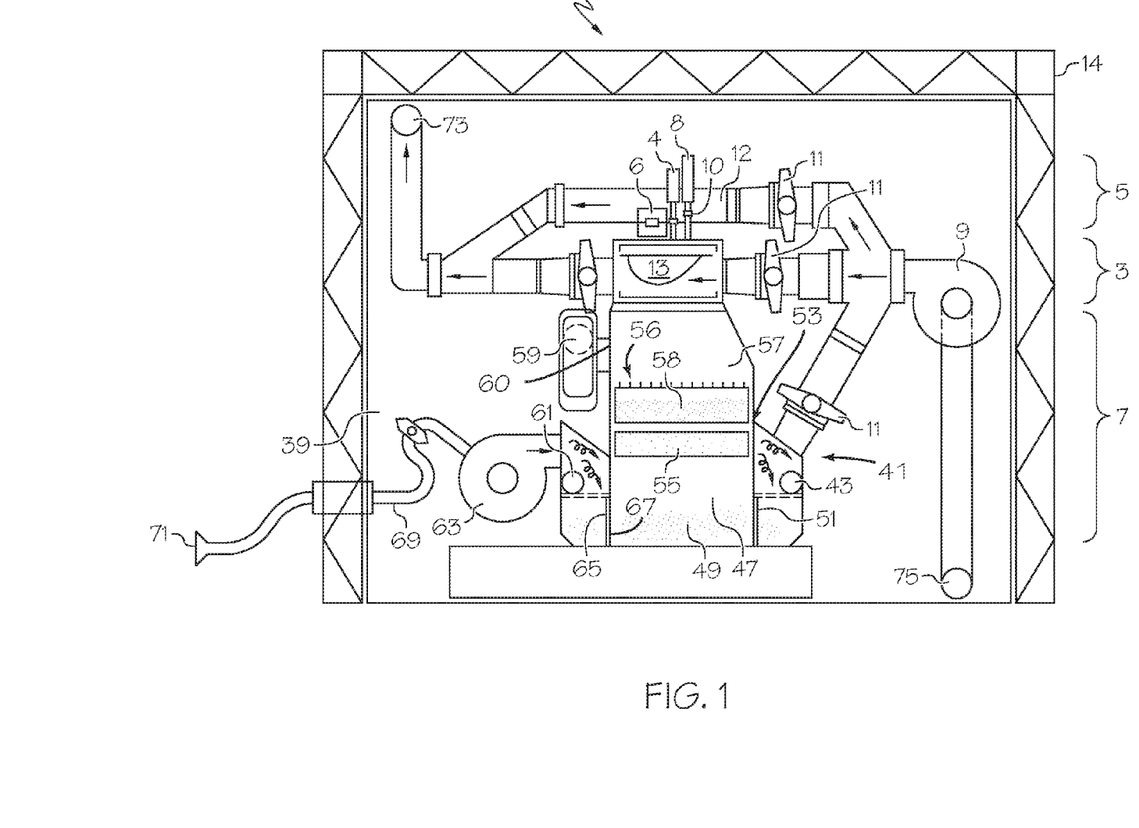
FIG. 1 depicts a cross-sectional schematic view of an exemplary combined activating area, bypass area, and neutralizing area; all operationally connected and contained in a single cabinet.

FIG. 1 sets forth an exemplary aspect of a decontamination system 1: a chlorine dioxide ($ClO_2$) fumigant activating area 3, a by-pass flow area 5, and a neutralizing area 7. A first variable speed air blower 9 is in direct fluid communication with the $ClO_2$ fumigant activating area 3, the by-pass flow area 5 and the neutralizing area 7. As illustrated, the activating, bypass and neutralizing areas may be housed in a single sealed container or "cabinet." Variable speed is advantageous in order to adapt the flow speed to particular decontamination needs and environmental sizes and configurations. Further, where the blower is directed to the activating area relatively low flow force may be desirable in order to avoid degrading the $ClO_2$ and producing chlorine gas; whereas when flow is directed to the neutralizing area higher speeds may be desired in order to promote degradation of the $ClO_2$. The system further comprises a valve system 11 for dedicating air flow from the blower 9 to one or more of the areas 3,5,7.

The activating area 3 comprises an activation cup 13 configured to receive reagents for in situ generation of $ClO_2$ fumigant. The activation cup 13 is permeable to air; yet substantially impermeable to water and reaction by-products. The activation cup is flexibly suspended in the activation area 3 such that air flowing from the first variable speed air blower 9 into the activation area flows through and around the activation cup such that generated $ClO_2$ fumigant passes out of the activation cup 13 with the air flow while water and reaction by-products remain in the activation cup 13.

Figure 2A:
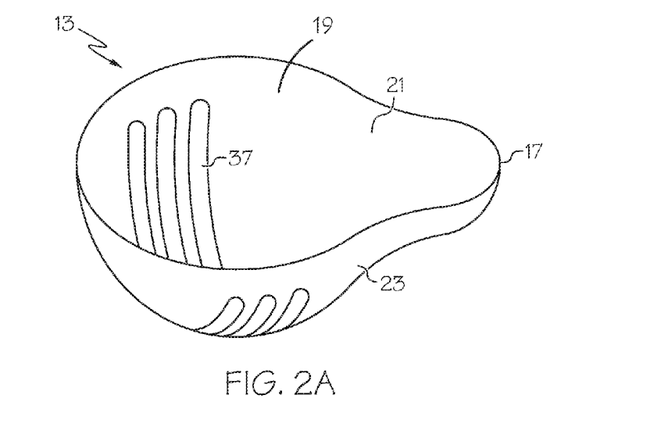
Figure 2B:
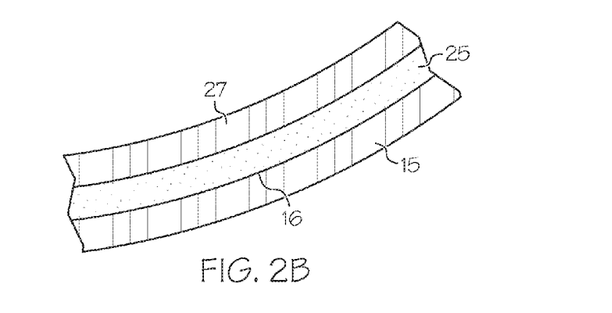
FIG. 2B. shows a schematic cross-section of a thickness of an edge of the cup illustrating a filter layer disposed between two molded layers.

Referring now to FIG. 2A and FIG. 2B, according to certain embodiments the activation cup 13 comprises: an outer layer 15 of crush-resistant thermally bondable nonwoven fiber molded into a transversely bisected aerodynamically-shaped shell 17. The shell 17 is oriented in the activating area such that it is open at the top 19. As illustrated in FIG. 2B, the shell has an interior surface 21 and an exterior surface 23 and at least one filter layer 25 interposed between the molded outer layer 15 and a molded inner layer 27. At least one filter layer 25 is adjacent and adherent to an inner surface 16 of the outer molded layer 15. The cup also has an inner molded layer 27 of crush-resistant fibrous material that is adjacent and adherent to the at least one filter layer 25. The at least one filter layer 25 is fabricated from a high-loft electrically charged polymeric microfibers. "High loft" is understood in the art to mean a fiber structure that contains more air than fiber. In more specific embodiments, the polymeric fibers comprise electret charged fluorinated melt-blown polyolefin microfibers having an effective fiber diameter of between about 0.5 µm and 12 µm, or more specifically between about 0.7 µm and 8 µm, or even more specifically having an average effective fiber diameter of about 1 µm. In particular embodiments, the air permeability of the fiber layer is between 80 l/m²/s and 8000 l/m²/s, and according to specific embodiments is between 100 l/m²/s and 1000 l/m²/s. Air flow resistance according to some embodiments is between 1.5 Pa and 100 Pa. Fibrous filter media suitable for embodiments of the invention are available from Hollingsworth & Vose of East Walpole, Mass.

Figure 2C:
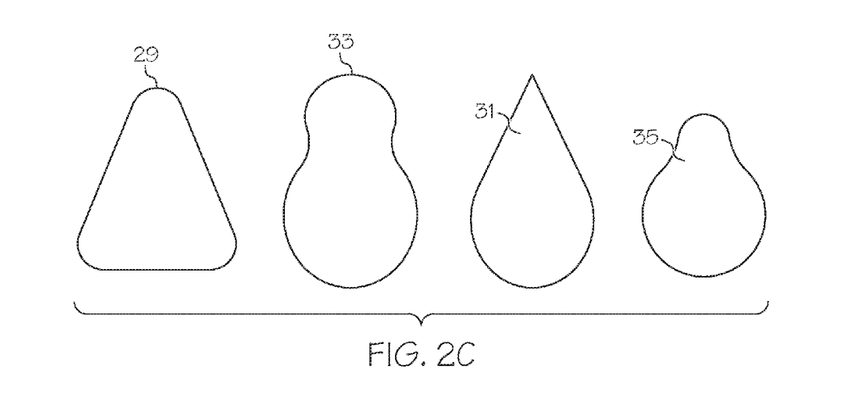
FIG. 2C, illustrates several shapes suitable as the aerodynamic horizontal cross-sectional shape of the top perimeter of an activating cup.

As shown in FIG. 2C, according to some embodiments the shell has a generally aerodynamic shape as defined from the front to the rear, the front being the leading edge of the air flow. Nearly any shape resulting in a substantially laminar flow of air around the contour of the shell is suitable. Non-limiting examples of suitable shapes of the horizontal cross-section of the shell include a substantially triangular shape 29, a teardrop shape 31, a pear shape 33, an aerofoil shape, or a saddle shape 35. In a very specific embodiment, the shape is saddle-shaped.

According to some embodiments, the exterior surface 23, or both the exterior surface 23 and the interior surfaces 21, of the shell 17 include a pattern of corrugations 37 effective to create turbulence in the airflow around and through the cup 13 resulting in vibration of the cup 13 and accelerated activation of $ClO_2$ fumigant. Any pattern of surface features is suitable; however generally the patterning should be symmetric about a horizontal axis lengthwise through the shell in order to avoid excessive agitation.

The activation area 3 comprises a series of conduits for addition of water, reagents and neutralizing solution to either the activation cup or directly into the air flow. The conduits include a first conduit 4 adapted for controlled metered addition of water to the activation cup 13, a second conduit 6 adapted for addition of dry reagents to the activation cup 13, and a third conduit 8 adapted for addition of neutralizing reagents to the activation cup. Any commercially available dry reagents for the production of $ClO_2$ are suitable. In specific embodiments, the dry reagents are added as a tablet, for example, a tablet comprising sodium chlorite and sodium Dichloroisocyanurate dihydrate. Inorganic acids and inorganic salts may also be included. Suitable dry-reagent tablets activated to produce $ClO_2$ upon addition of water are available from Quip Laboratories, Inc. of Wilmington, Del.

The conduits 4 6 8 may be controlled by ball-valves 10 which may be opened and closed by manual turning, or by automated turning achieved without manual touching. In some embodiments, the by-pass area 5 comprises at least one conduit 8 in communication with a pipe or tube traversing the by-pass area 5 for addition of neutralizing reagents directly to the air flow.

The neutralizing area 7 comprises two distinct functional spaces—a leak abatement space 39 and a $ClO_2$ fumigant neutralization space 41. Although the neutralizing space will be described as a series of treatment centers in sequential order, it is understood that any additional treatment stations may be included at any point as determined by particular needs. Air flow may be directed into the neutralizing space by valve manipulation. The $ClO_2$ fumigant neutralizing space 41 comprises: a first treatment station 43 comprising ultraviolet light (UV). According to specific embodiments, the inside of the UV treatment center includes a UV light source and a reflective interior surface to increase exposure of the $ClO_2$ gas to the UV light in the station. The UV treatment station is contained within a compartment that may be irregularly shaped to further increase disruption in the $ClO_2$ air flow, which results in increased dwell/residential time in the UV station. In some embodiments, the variable speed blower is positioned to direct fumigant air flow to a wall of the UV compartment, further creating disruption in the flow and UV exposure dwell time. The user is protected from exposure to the UV light since the system is contained within a sealed opaque container, such as a cabinet. In very specific embodiments the UV light is designed to turn off when the cabinet is opened.

The first treatment station 43 is in operational communication with a variable air blower 45. Generally, when the activating area and neutralizing area are housed together, a single variable air blower with dedication capability comprising, for example, flow valves, may be utilized, although this is not always necessary. In embodiments where the activating area and neutralizing area are contained separately, different variable air blowers may be employed for the activating versus neutralizing functionality. It is clear that various configurations of air blowers may be utilized without departing from the spirit of the invention. In comparison to the relatively low flow force generated by the air blower for activation functionality, the air blower 45 is set to blow fumigant waste air at a relatively high speed through the first treatment station. "High" in this context is defined as at a force sufficient to agitate and degrade $ClO_2$ present in the fumigant waste air, thereby resulting in partially treated air. The air flow from the variable air blower 45 is directed to an interior surface of the UV station compartment in order to create flow disturbances as the air flow passes into the second treatment area. Partially treated air may include both ClO2 and degradation products of $ClO_2$.

Upon exiting the first treatment center, the now-disrupted air flow enters a second treatment station 47 comprising a reservoir 49 of liquid neutralizing solution. $ClO_2$ neutralizing solutions are known in the art. According to a preferred embodiment, the neutralizing solution comprises sodium thiosulfate and water. In some embodiments a diffusion plate 51 or baffle separates the first and second treatment stations. As the disrupted flow is forced into the neutralizing solution reservoir 49, frothing and bubbling and formation of turbulent flow features such as eddies occurs, further aiding the neutralizing process effectuated by the neutralizing solution, both by agitation and the extended residential time in the reservoir that results. In some embodiments the reservoir 49 is separated into at least three chambers (not shown). Diffusion plates or baffles may be utilized to separate/create the chambers, however, all chambers contain the neutralizing solution reservoir. The second chamber, which in preferred embodiments is also the largest chamber, is the chamber from which air flow enters the third treatment center, such as third treatment center 53 described below. The second chamber is positioned between the first and third chambers. The first chamber is in direct communication with the first treatment center 41 and the flow passes into the first chamber at an angle, causing disruptions in the flow. The third chamber on the opposite side of the second chamber from the first chamber is positioned to receive air flow from the leak abatement space 39 powered by another blower 63 functioning as a re-circulation blower. A person of ordinary skill in the art will realize that additional configurations of chambers designed to promote turbulence and thereby increase the rate of the neutralization reaction in the reservoir may be utilized. Generally, more chambers results in greater turbulence and reaction mechanics favoring enhanced neutralization.

The waste fumigant air leaves the second treatment center 47 as substantially treated air. As used herein, "substantially treated" means that only residual amounts of $ClO_2$ may remain in the air flow. The solution in the reservoir is bubbling and frothing from the flow disruptions and forced flow through diffusion plates into the reservoir. The second treatment station is in communication with a third treatment station 53 comprising a humidification filter 55 positioned over the reservoir 49. The humidification filter 55 is configured to capture, contain and return neutralizing solution to the reservoir while permitting substantially treated air to pass through. In specific embodiments the humidification filter 55 is fabricated from open-celled polymeric material. Localized high concentrations of neutralizing liquid may form in some of the cells, further providing enhanced neutralization capacity. According to specific embodiments, the humidification filter 55 comprises a humidification pad and humidification fins. In more specific embodiments the humidification fins comprise grooves bd. Generally the fans are aligned above the reservoir 49 and beneath the humidification pad.

As the air flow passes through the third treatment station it enters a fourth treatment station 56 comprising coated zeolite 58. The zeolite 58 may be coated with sodium thiosulfate or another suitable $ClO_2$ degradant or neutralizer. Specific organic materials are known in the art as effective coatings for neutralization of $ClO_2$. In other specific embodiments calcium hydroxide may be coated over the zeolite to remove carbon dioxide.

In some embodiments a treatment station 57 comprising activated charcoal suitable for removing odiferous molecules from the treated air may be included. For example, sulfur gas may be present in the treated air. The activated charcoal may be sprinkled into the zeolite or may form a layer over the zeolite, or may in some aspects be a layer distinct from the zeolite. It is an important consideration to the design of the neutralizing area that the waste fumigant is not contacted with a carbon-based filter until after the $ClO_2$ has been neutralized so as to avoid a fire hazard resulting from localized $ClO_2$ concentration build up in the spaces and pores of carbon filtration media.

According to some embodiments, the leak abatement space 39 comprises: a blower 59 adapted for pulling treated air through an exit port 60 of the neutralizing space 41 and into the leak abatement space 39. This blower acts as a pull-blower and also aids in creating circulation of air in the leak abatement space to ensure that any leaks into the internal space of the cabinet are dispersed and re-circulated into the neutralizing space. A fifth treatment station 61 comprising UV light is located in the leak abatement space. A second variable air blower 63 is positioned to blow air from the leak abatement space 39 through the fifth treatment station 61 and into a chamber of the reservoir 49 at high speed. In some embodiments, the air flow from the fifth treatment station is disrupted by directing the air flow from the blower 63 at an oblique angle to a containment wall of the UV treatment space such that it enters the chamber of the reservoir as a disrupted air flow, creating turbulence and eddy formation in the reservoir. A second diffusion plate 65 or baffle may be positioned at an interface 67 between the fifth treatment center 61 and the reservoir 49 to create bubbling and frothing in the reservoir. As used herein, "high" flow rate is defined as sufficient to agitate and degrade $ClO_2$ present in the leak abatement space 39.

In some embodiments the leak abatement 39 space may be connected to an environment external 71 to the sealed housing by one or more hoses 69 including at least one hose connected to the variable speed blower 63 to provide a vacuum force effective to pull potentially contaminated air from the external environment 71 and direct it into the fifth treatment station 61. A user may immediately decontaminate the external environment where a leak is indicated by one or more sensors located in the external environment by utilizing the vacuum hose. The air blowers of the system are sealed and configured to operate on direct-current power for safety. Ventilation blowers designed for marine (boating) use are suitable as the blowers of the decontamination system because they are sealed to the immediate environment and water/moisture resistant. Such blowers are available from a number of suppliers including Attwood Marine Products, Inc.

According to some embodiments, the activating area 3 and neutralizing area 7 may be housed together in one sealed housing 14, for example in a cabinet. In other embodiments the areas may be housed separately in independent sealed housings. In particular embodiments suited for decontamination of buildings via the HVAC system, multiple independently housed activating areas 3 may be employed throughout the building along with at least one neutralizing area 7. The cabinets, whether housing independent activating or neutralizing areas or combinations thereof, may include wheels for simply portability, or other portability means (handles, pull handles and the like). In this way the decontamination system may be configured as a modular and portable system. Further, systems may be converted readily from closed to open systems by manipulation of sealed valves placed within the system piping.

According to some embodiments, the activation area 3 and neutralizing area 7 are housed together in one sealed housing 14 and the system further comprises a separate decontamination chamber 77. The sealed housing comprises a $ClO_2$ fumigant outlet port 73 and a $ClO_2$ waster air inlet port 75. The decontamination chamber 77 is scalable and configured to hold a product 79 to be decontaminated and comprising an inlet port 81 sealingly connected by a positive flow line to the $ClO_2$ fumigant outlet port 73 and an outlet port 84 sealingly connected by a negative flow line to the $ClO_2$ waste air inlet port 75 to form a closed loop decontamination system 85. As shown in FIG. 3, the sealed housing 14 may be fitted with wheels 96 for portability.

Specific size, dimension, and functionality of decontamination chamber 77 will vary according to the decontamination needs. The chamber may be scaled down for small articles or scaled up for very large articles and may be made collapsible for portability needs. According to some embodiments, and with reference to the exemplified embodiment of FIG. 3, the chamber comprises an inner containment structure 87 and an outer “skin” 89 and has an air space 91 between the inner containment structure 87 and outer skin 89. The inner structure 87 and outer skin 89 are fabricated from a fire and blast retardant material and may include an anti-static coating on surfaces contemplated as being operationally contacted with $ClO_2$ fumigant or $ClO_2$, waste air. In other specific embodiments all piping and tubing of the system through which $ClO_2$ traverses comprise a static-resistant material. Further, the decontamination system is grounded and utilizes DC current/batteries to avoid realizing an ignition risk associated with $ClO_2$ gas.

In some embodiments, the decontamination chamber further comprises at least one air blower 93 positioned to inject air in the air space 91, wherein the at least one blower 93 is sealed and operates on a direct current. The chamber 77 may include one or more doors 95 and a blower 93 may be positioned in proximity to each door 95. In very specific embodiments the decontamination chamber is constructed to be erected and collapsed by the use of ambient air. In particular air may be pumped into support tubes arranged along the periphery, the tubes become rigid and pull the fabric of the chamber as they expand, thus erecting the chamber. As shown in FIG. 3, the air blower 93 may be fitted with wheels 96 for portability.

The inventive decontamination system is particularly suitable for decontamination of a building 150 or contained area within a building via the ductwork of the building's HVAC system 97, which also serves to decontaminate the HVAC system. Residual contamination present in HVAC duct work is responsible for recontamination of decontaminated buildings where the decontamination methods fail to account for it. In this application, the decontamination system is configured as an open-loop system with activating areas (referred to as activators) connected to neutralizing areas (referred to as neutralizers) by connections to the building's HVAC system 97 comprising an HVAC unit 99 and HVAC duct work 100. At least one activating area 3 is in fluid communication with a neutralizing area 7 via the HVAC duct work. Referring to an embodiment illustrated by FIG. 4, multiple independently housed activating areas 3 are located in the building relative to the HVAC unit 99 such that gravity aids in distribution of $ClO_2$ fumigant through the duct work 100. The number of activators should correspond to the size of the building and the number of rooms into which the floor or building is divided, as well as the desired target concentration of $ClO_2$. The optimization of a particular configuration of the system will be readily apparent to one of skill in the art.

Figure 3:
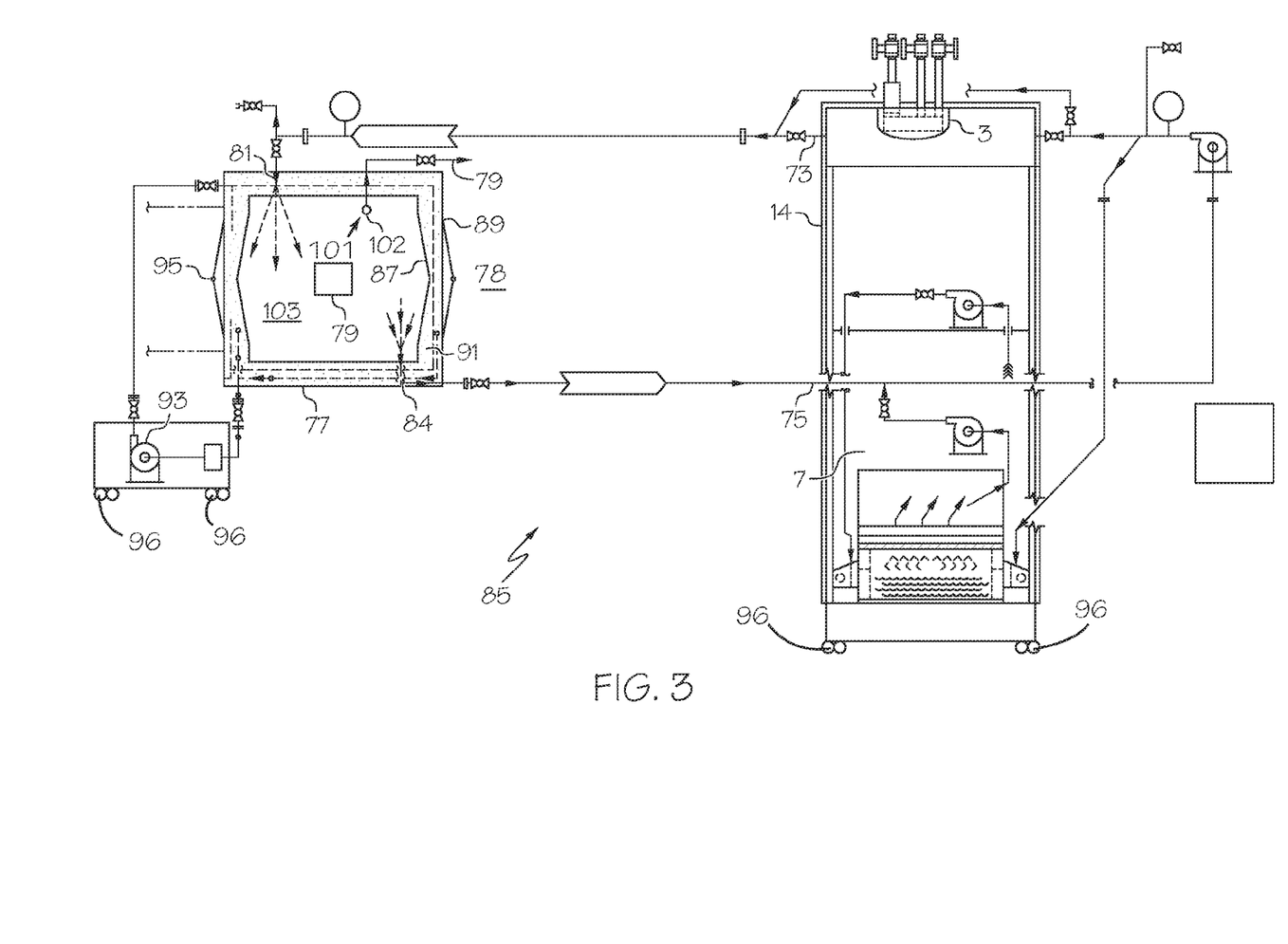
FIG. 3 sets forth an exemplary schematic representation (not scaled) of a closed loop system including activating and neutralizing areas which may or may not be combined into a single contained unit, operationally connected to a decontamination chamber.

A series of sensors and read-outs may be utilized to monitor the $ClO_2$ concentration throughout the decontamination and neutralizing cycles. Where a decontamination chamber is utilized, concentration of $ClO_2$ fumigant in the decontamination chamber 77 is monitored by a monitoring device 101. The device comprises at least one $ClO_2$ sensor 102, which may be located in an interior space 103 of the decontamination chamber 77 or external to a sampling port 79 in communication with the interior space 103 of the decontamination chamber 77. $ClO_2$ fumigant leakage may be monitored by one or more monitoring devices comprising $ClO_2$ sensors 102 located in a space exterior 78 to the decontamination chamber 77 or exterior to any of the modular components according to particular embodiments of the invention. Suitable sensors and monitors are well known in the art and available from multiple manufacturers.

Embodiments of the invention also include methods based on utilizing the inventive system technology, either as individual components or in any modular configuration of components. Methods for generating chlorine dioxide fumigant in a directed flow with a minimum of water comprise providing an activation cup according to embodiments of the invention and directing an air flow through the cup. According to specific embodiments, the cup comprises an outer layer 15 of crush-resistant thermally bondable non-woven fibers molded into a transversely bisected aerodynamically-shaped shell 17 where the shell 17 is open at the top 19 and has an interior surface 21 and exterior surface 23. The exterior surface 23 and interior surface 21 may include a pattern of corrugations 37 to create turbulence in the air flow such that the reaction mechanics are enhanced to increased production of fumigant. The cup comprises at least one filter layer 25 interposed between the outer molded layer 15 and an inner molded layer 27 and including one filter layer adjacent and adherent to an inner surface 16 of the outer layer 15. The filter layer may comprise multiple layers, however at least one layer 25 comprises high-loft electret charged fluorine-coated polyolefin microfibers such that the activation cup 13 is adapted to retain water and reaction by-products while permitting gas to pass through, directed by the air flow. In specific embodiments, the cup is flexibly suspended in the air flow. Dry reagents for production of $ClO_2$ fumigant are added to the cup 13 and the directed air flow is initiated. Corrugation patterns in the cup create mild turbulence in the flow resulting in a slight vibration of the cup. "Corrugation" herein is meant to include any surface feature that disrupts air flow. It is an important consideration to keep the air flow speed low during this process to avoid degrading $ClO_2$, which is a relatively fragile molecule. The addition of water to the cup initiates generation of $ClO_2$ fumigant that is directed out of the cup 13 with the air flow while water and $ClO_2$ generation reaction by-products are substantially retained in the cup 13. Analysis of the resultant $ClO_2$ fumigant flow reveal that it is comprised almost entirely of $ClO_2$ fumigant without a significant presence of water or acid vapor.

Although the activation cup aspect is described herein in relation to generation of $ClO_2$ fumigant, it is contemplated that the cup would provide similar benefits with respect to the in situ generation of any chemical gas.

Embodiments of the invention further include methods for neutralizing fumigant chlorine dioxide ($ClO_2$) in a sealed neutralizing area 7. The neutralizing area 7 comprises a leak abatement space 39 and a neutralizing space 41, and the neutralizing space 41 comprises a series of treatment stations and at least one blower. Methods may include the liquid neutralizing solution reservoir treatment station in combination with at least one additional treatment station described herein. A preferred embodiment includes the UV 43, neutralizing solution 47, humidification filter 53, and zeolite 56 treatment stations in sequential order. In some embodiments the method comprises blowing $ClO_2$ fumigant to-be-neutralized into a treatment station comprising ultraviolet light, resulting in partially neutralized air. The blowing is effectuated at a speed high enough to degrade $ClO_2$. The air flow is directed to hit a compartment wall of the UV station at an oblique angle in order create disruptions in the air flow as it enters the liquid neutralizing solution reservoir. The partially neutralized air from the UV treatment station may be blown through a diffusion plate 51 and into a treatment station comprising a liquid neutralizing solution reservoir.

The reservoir may be divided into chambers (not shown) separated by diffusion media in the form of plates or baffles, resulting in bubbling and frothing in the reservoir and enhanced neutralization reaction mechanics and degradation, resulting in substantially neutralized air. In a preferred embodiment the liquid neutralizing solution comprises sodium thiosulfate and water. In specific embodiments bubbled solution is captured and returned to the reservoir by a treatment station 53 comprising a humidification filter 55 that permits the substantially neutralized air to pass through the filter. In further specific embodiments the substantially neutralized air then passes into a treatment area 56 comprising coated zeolite 58 (coated with one or more of sodium thiosulfate and calcium hydroxide) to neutralize any remaining $ClO_2$ and to remove other toxic gaseous by-products remaining in the substantially neutralized air, resulting in neutralized air; and, optionally, passing the neutralized air through activated carbon to remove odiferous molecules which may be present in the neutralized air. The activated carbon may be in particle form intermixed with the zeolite, or sprinkled over the top of the zeolite layer, or may form a distinct layer through which the neutralized air passes.

The neutralized air is then pulled into the leak abatement space 39 by a blower 59 acting as a pull blower, where it may be circulated in the leak abatement space and recirculated through the neutralizer by a variable speed blower 63 directing air from the leak abatement space into the neutralizing space 41 and through another UV treatment station 61. A valve controls whether or not recirculation is effectuated. Leaks detected on the outside of the sealed housing 14 by sensors/monitors (such as sensors 102 in FIG. 3) may be vacuumed into the leak abatement space by one or more hoses 69 sealingly connecting the leak abatement space to an environment 71 exterior to the housing. The re-circulation loop is opened and contaminated air is pulled through the variable speed blower directing it into the UV treatment center 61 and into the reservoir 49 as described earlier.

The decontamination system of the present invention may be configured into a specific embodiment, such as shown in FIG. 3, having utility for sterilization and transportation of sterilized product in a single chamber. In this embodiment the "decontamination chamber" 77 is the transported chamber and a closed loop is formed with a combined activator/neutralizer unit 14 by connecting outlet port 73 of activation area 3 with inlet port 81 of decontamination chamber 77 and outlet port 84 of decontamination chamber 77 with inlet port 75 of neutralizing area 7 as described herein. An article 79 in need of decontamination is placed into the decontamination chamber 77 and the method comprises generating $ClO_2$ fumigant and directing the generated $ClO_2$ fumigant through the closed loop to achieve a concentration of $ClO_2$ fumigant in the decontamination chamber across a time frame sufficient to achieve target sterilization of the product. The concentration may be monitored and affirmed by at least one $ClO_2$ concentration sensor 102. Once the target concentration is reached and held for the target residential time, the decontamination chamber 77 is decoupled from the sealed housing 14 while maintaining sealing of the decontamination chamber from the environment. The sterilized article is then transported to a target destination in the chamber. It is contemplated that the decontamination chamber in specific aspects of this embodiment may be adapted to suitcases, trunks, coolers, medical containment cabinets, and the like.

With reference to FIG. 5, a specific application illustrating use of a decontamination system according to certain embodiments of the invention to provide and maintain a sterile operating room environment is described. $ClO_2$ gas is theoretically an ideal sterilant for this environment, which contains a wide variety of substrates. A safe and effective system for providing a target concentration to an operating area of an operating room has heretofore not been developed.

Figure 5A:
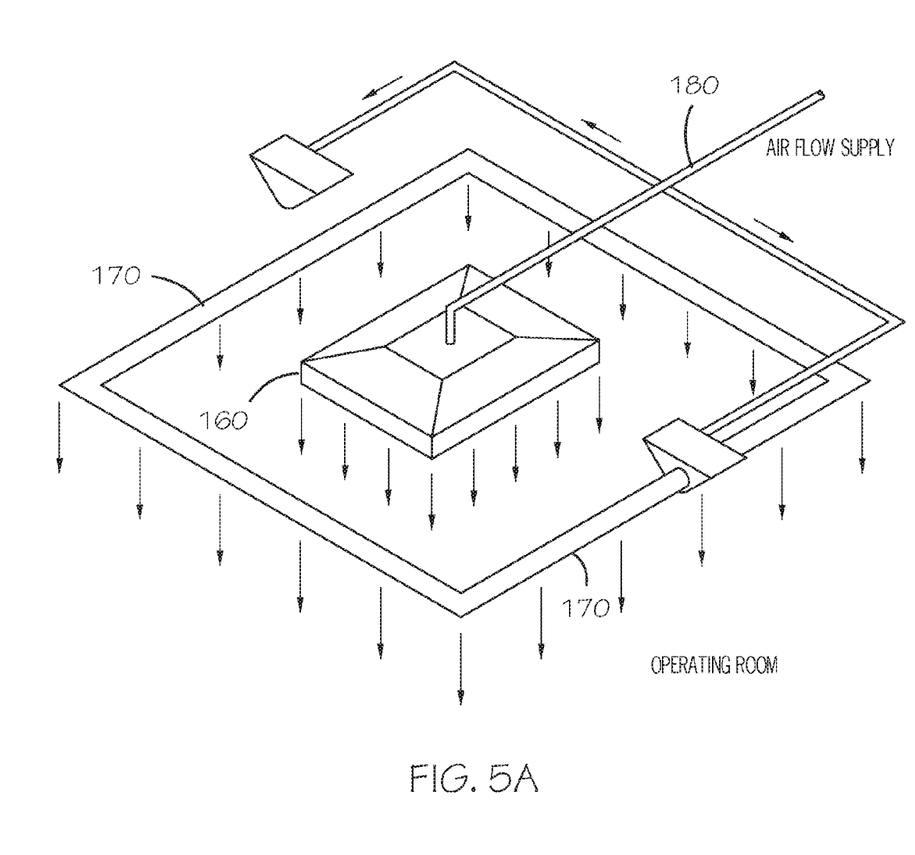
Figure 5B:
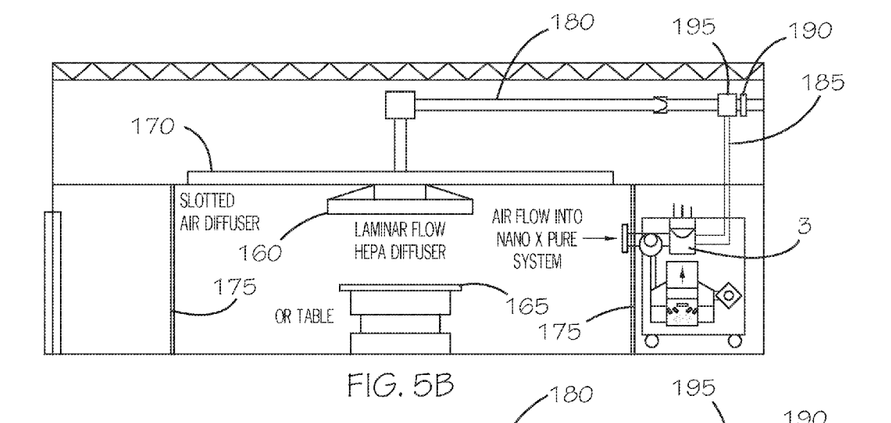
FIG. 5B. shows a schematic representation of the operational combination of the decontamination system with the operating room via the HVAC system.
Figure 5C:
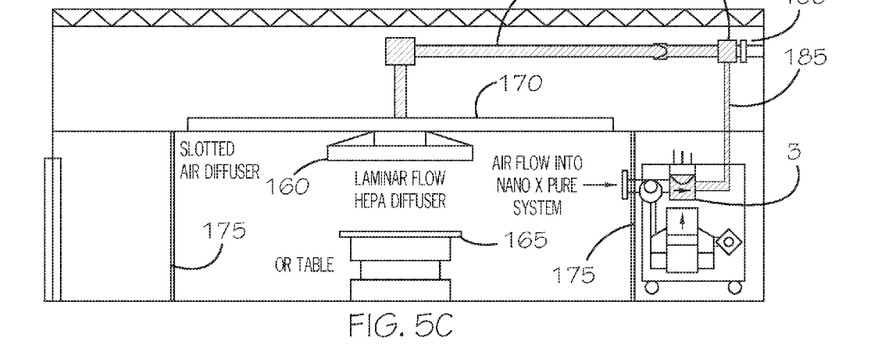
FIG. 5C. illustrates generation of $ClO_2$ fumigant and flow into the air supply duct via an access port and then over the operating room via the HVAC system.
Figure 5D:
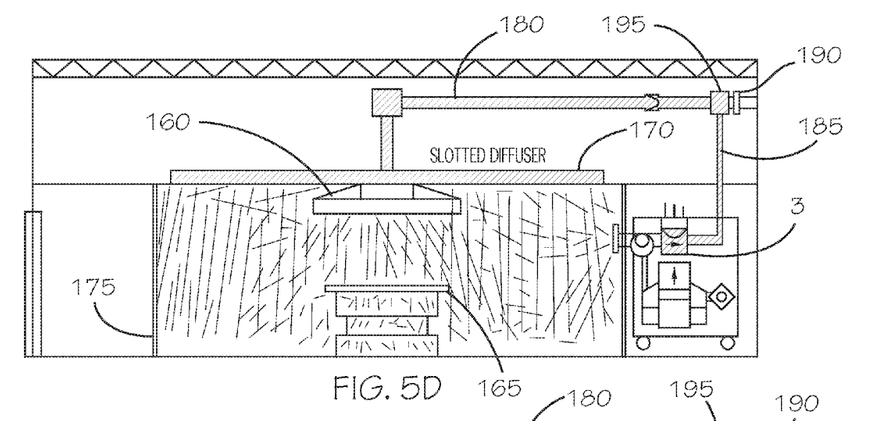
FIG. 5D, shows the fumigant diffused into the operating room and contained within the air curtain.
Figure 5E:
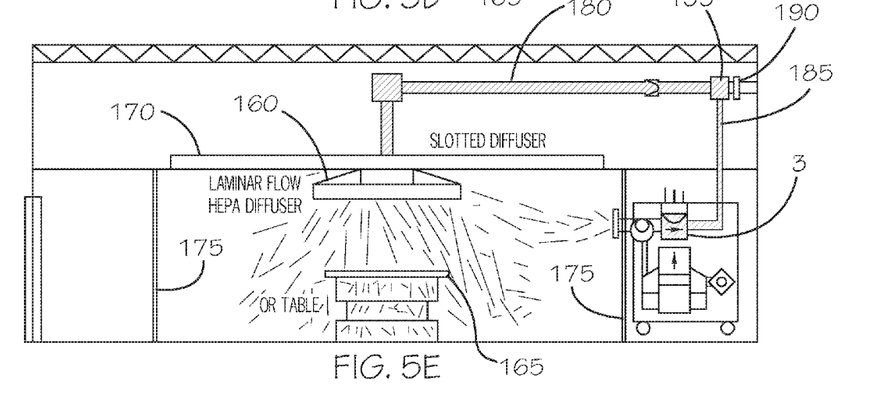
FIG. 5E, shows the fumigant directed into the decontamination system where it may be neutralized or re-circulated depending on valve manipulation and need.

$ClO_2$ gas is activated in a system activator 3 as described above. With reference to FIG. 5A, the system comprises a laminar diffuser 160 comprising a HEPA diffuser is set over the operating table 165 area, and one or more slotted diffusers 170 set up around the periphery of the operating table area. The diffusers are in communication with the room's air supply duct work 180 connected to the main HVAC system knot shown). A temporary plastic wall 175 is installed to section off an operating room area just outside the contemplated air curtain. A conduit 185 from the activator to the air duct supply is set up so that $ClO_2$ fumigant may enter an air supply duct of the room. A damper 190 in the air supply duct is installed if not already present, in order to seal off the OR's air supply. An access port 195 to the decontamination system is installed downstream from the damper. The damper is closed. Air from the air supply duct is directed through the laminar diffuser and the slotted diffusers, forming a $ClO_2$ air curtain around the operating area. FIGS. 5B though 5E show how the fumigant is distributed and dispersed into the OR. When the decontamination need ceases, a valve may direct the air from the operating room area to the neutralizer. Re-circulation enhances the neutralization process.

Target concentration may be determined by decontamination needs and regulatory requirements for particular environments. The decontamination system as described herein is capable of reaching and maintaining sterilization conditions for a variety of substrates.

The following Examples are presented to illustrate and clarify certain aspects and embodiments of the invention and should not be construed to limit the full scope of the invention as defined by the appended claims.

For purposes of the Examples, dry reagents for $ClO_2$ were provided as MB-10 6 gm tablets (available from Quip Laboratories, Inc. of Wilmington, Del.). Each tablet contains 25-35% by weight inorganic acid, 35-45% inorganic salt, 15-24% sodium chlorite, and 5-10% by weight sodium dichloroisocyanurate dihydrate.

Example 1

This example illustrate an embodiment directed to activation of chlorine dioxide in the activation cup and demonstrates that $ClO_2$ gas is produced and directed through the cup, while water and reaction by-products and salts remain contained within the activation cup. A well-known problem in the art of $ClO_2$ decontamination systems is that production of the gas in water from dry reagents involves corrosive salts as a byproduct of the reaction. The salts shorten the life of delivery and dispersal equipment. Another well-known problem is the amount of water typically present in the $ClO_2$ fumigant, since water is necessary to catalyze the $ClO_2$ production reaction. This is particularly problematic where corrosion-sensitive articles such as electronic devices are in need of treatment. Prevention of dispersal of the salts as well as minimization of water in the treatment air flow is therefore highly desirable.

The filter layer of a specific activation cup embodiment was fabricated of polymeric microfibers comprise electrat charged fluorinated melt-blown polyolefin microfibers having an effective fiber diameter of about 0.7 µm. The shell itself was formed by layering the filter material between layers of the crush-resistant thermal molding polymer and press-molding under temperatures sufficient to mold the outer and inner layers; however lower than the melting point of the fiber layer. This is essentially the same technology utilized in the respirator industry to fabricate face-worn respiration masks to protect the wearer from inhaling particles other than gas molecules, and for trapping exhaled moisture in the apparatus to prevent excessive build-up and inhalation of moisture by the wearer.

Two MB-10 tablets were activated with 30 ml water in the activation cup. The total weight of the cup, water and tablets was 50.6 g. Gas was blown with a variable air blower through the cup and into a 36 cu. ft. stainless steel tunnel. Electronic equipment was placed in the tunnel. Gas concentration was verified by ATI Porta Sens gas detector through ports in the chamber.

Gas concentration reached 240 ppm and was held for 6 hours. Total weight of activation cup and contents after cessation of reaction was 45.1 gm; hence approximately 5.5 g $ClO_2$ gas was produced. The activation cup was dried and inspected. By-product salts were found trapped in the bottom of the activation cup and in the filter later. Neither the fan nor the computer equipment showed any effect from the gas.

Example 2

This example illustrates operation of one embodiment of the decontamination system using recircualtion to aid in the penetration of the $ClO_2$. Demonstration of partial neutralization of $ClO_2$ with ultraviolet light was confirmed.

A roll of moldy filter material having an approximate volume of 7 cu. ft. and exhibiting a moldy odor was placed into a 36 cu. ft. stainless steel chamber. The decontamination system cabinet was fitted with an inlet and an outlet port for recirculation. Two MB-10 tablets were activated utilizing the activation cup in accordance with Example 1, and gas concentration in the chamber was monitored by an ATI Porta Sens detector. Two biological indicators were placed about 4 inches inside the roll on either end and five Rodac plates were used to sample every 20 ft. when the material was unrolled. The gas was held for three hours and reached a maximum concentration of 661 ppm. After the decontamination period was over, the $ClO_2$ gas was neutralized with UV light and gas remaining in the chamber was sampled every 5 min. The biological indicators and Rodac plates were sent to Air Filter Testing Labs for verification of results.

The results showed no growth in the biological indicators or the Rodac plates. The moldy smell was no longer perceptible, indicating sterilization. The UV light dropped the gas concentration about 8 to 14 ppm every 5 min., which is relatively slow but effective. Recirculation enhanced the penetrating ability of $ClO_2$ and the process sterilized the entire roll.

Example 3

This example illustrates an aspect of the system comprising a collapsible decontamination chamber fabricated of fire and blast retardant material with an air layer created between an inner scaffold and an outer layer. The volume of the chamber was about 300 cu. ft., which is the volume necessary, for example, to contain a complete hospital bed or around ten standard-sized hospital mattresses. The entire decontamination system was designed to be portable. This example also illustrates that recirculation is an effective alternative to 24 hour evacuation in off-gassing environments.

An office chair of faux leather, end table, hospital bed, and a roll of filter material were placed in the decontamination chamber in order to provide data on a range of materials and surfaces. Two biological indicators were used, one inside the drawer of the table and the other placed about three feet inside the roll of filter material. Two MB-10 tablets were activated in the activation cup spaced 70 min. apart in order to illustrate boosting gas concentration. The gas was recirculated through two openings fitted at the end of the chamber. The test ran for three hours and an ATI Porta Sens used to monitor gas concentration.

Fumigant gas concentration reached 93 ppm, and then started to drop. The second tablet boosted the concentration to 226 ppm. Biological indicators showed negative growth indicating sterilization. When the monitor read zero, the fan was turned off; however the monitor showed that the $ClO_2$ gas concentration rose back to 10 ppm after several minutes. This is the result of absorbent material in the chamber off-gassing absorbed $ClO_2$. The fan was restarted and set to high, and the remaining $ClO_2$ was evacuated in ten minutes as confirmed by monitoring.

Example 4

This example illustrates safe control of $ClO_2$ gas indoors in a confined space. The test embodiment of the neutralizing area included a neutralizing solution of sodium thiosulfate along with a finishing filter composed of zeolite coated with sodium thiosulfate plus carbon granules atop the zeolite layer to trap any residual odors. The whole system comprised two loops, one that delivered the gas into the chamber to effectuate decontamination. The second loop was an internal loop that swept any escaped gas past a UV light back into the neutralization solution as a safety feature. The system was contained in a medical grade cabinet on wheels for easy portability.

Two MB-10 tablets were used to produce a gas concentration of 72 ppm at the highest concentration point. Biological indicators were placed inside the collapsible decontamination chamber at the entering and exiting portals. The valves were manipulated and the data demonstrated that opening the valve a quarter turn on the intake side while opening the neutralization valve resulted in effective one-pass neutralization. The ATI Porta Sens detector was again used to monitor gas concentration.

The results further demonstrated that during the initial surge some $ClO_2$ gas escaped inside the cabinet but was quickly swept into the neutralizing chamber (within two minutes). Biological indicators showed no growth of microbes. The entire process took about two hours with no gas detected outside the cabinet at any time. Activation fluid inside the activating cup was neutralized and brought to a safe pH of 7.

Example 5

This example illustrates sterilization of a laboratory incubator in a real-world context. Price Institute for medical research at the University of Louisville reported experiencing molding of tissue samples by an incubator contaminated with mold spores. Repeated attempts to disinfect the incubator failed.

A decontamination system according to one embodiment of the invention was taken on-site to the lab. The incubator measured 2×2×3 ft=12 cu. ft. It was assumed that the internal circulation of the incubating device had become infected with mold which could not be reached by conventional scrubbing. Ambient temperature was 72° F. and ambient humidity was 57%. Temperature of activation was 113° F. A bag attached to the decontamination system was taped over the door of the incubator with the door open. Two biological indicators were placed inside beforehand. One MB-10 tablet was activated and the generated $ClO_2$ fumigant was pumped into the incubator. The door was closed and taped. The gas was held overnight, the tape was removed, the bag was placed over the door and the door was then opened. $ClO_2$ gas was evacuated and neutralized. Neutralization took about ten minutes. Biological indicators were sent to Air Filter Testing Lab for third party verification of sterilization.

The biological indicators provided positive verification of sterilization and follow-up reports from the lab indicate that the formally chronic and intransigent contamination problem has resolved.

Example 7

This example, when taken with Example 6, illustrates scalability of the decontamination system. The Price Institute at University of Louisville reported a black mold growing in a walk-in cooler in lab 330. The cooler had a distinct moldy odor and contained several boxes and other items. It was requested that the mold be removed so that new tissue samples and sensitive research items could be safely stored without threat of contamination.

Three biological indicators were placed inside the cooler. One was placed at the top near the internal blower, one at the bottom near the floor, the other between boxes on one of the shelves. The cooler's blower was turned off and plastic sheeting was taped over the door opening. An entering hole and exiting hole were cut and the hose that delivered the $ClO_2$ gas was inserted and sealed with tape. A total of 6 MB-10 tablets were used two at a time until the gas concentration reached sterilization levels. The process lasted about two hours. The internal blower was turned back on just before we began neutralization of the gas.

The results demonstrated complete efficacy with respect to sterilization and the gas was neutralized with no leakage. The ability of the inventive decontamination system to remove black mold in a confined space without evacuation of the facility is a significant improvement over systems known in the art.

Example 8

Figure 4:
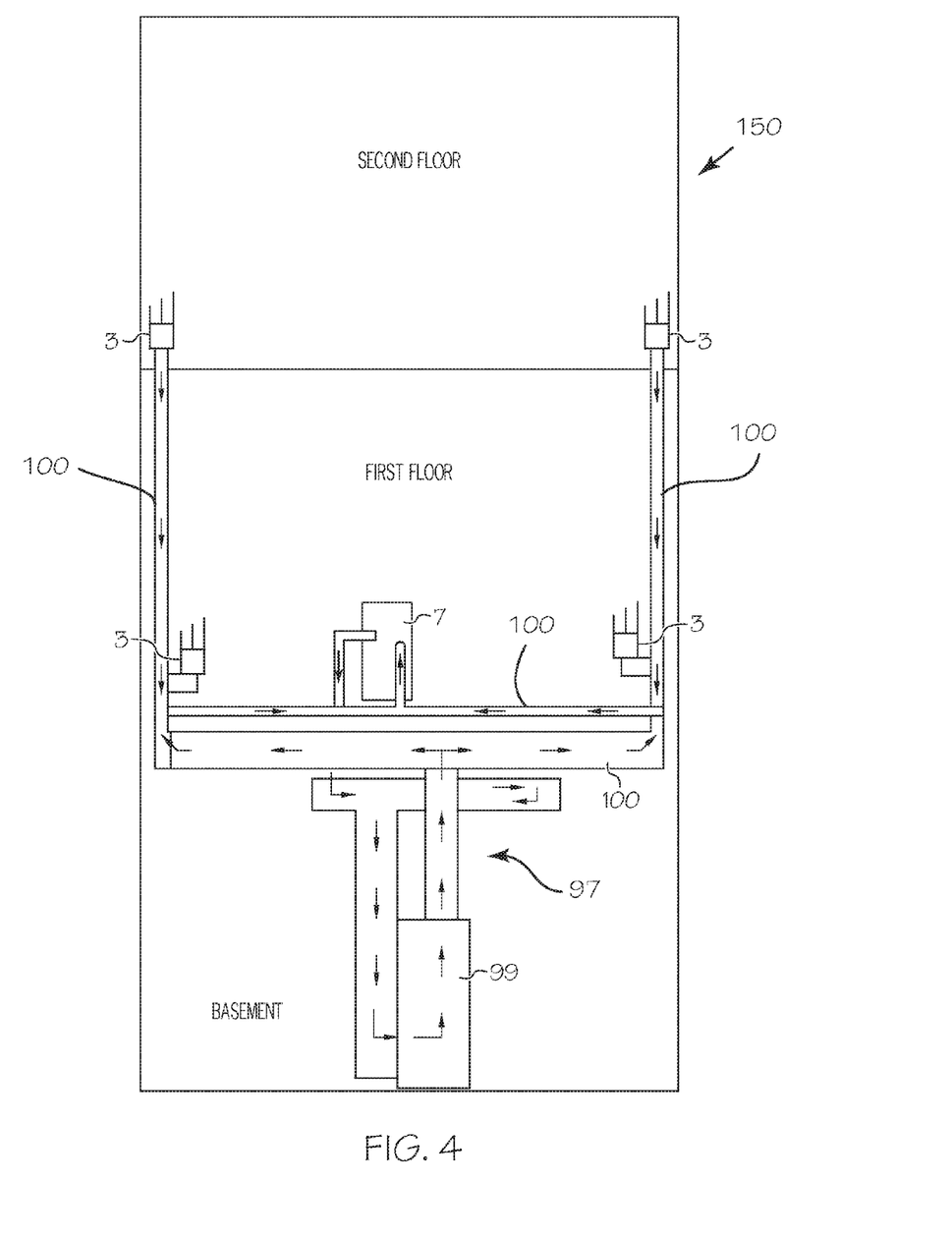
FIG. 4 sets forth a schematic representation of decontamination of a multiple-floored building where decontamination is via the HVAC system of the building and multiple additional portable activating areas are located on each of the floors over the HVAC unit location, all in communication with the main decontamination unit.

This Example illustrates decontamination of a 363 cu. ft. HVAC/duct space and the flexibility in implementing the modular/portable system for effective decontamination of multiple-story buildings. FIG. 4 illustrates a basic schematic of the design. Application of embodiments comprising multiple portable independent activation areas contained in, for example, rolling or easily transportable cabinets, is contemplated for convenient decontamination/sterilization of hospital rooms. It is critical to clean air ducts coming into the room or once air is resumed, the room may become re-contaminated. A very specific application of this embodiment relates to sterilization of operating rooms as illustrated schematically in FIG. 5.

HVAC ducts often have 90 degree turns and multiple pathways, which poses challenges for air flow being pushed from a central area into all reaches of the system. For example, multiple story homes may be difficult to air-condition with a single down-stairs unit. In order to avoid this, and to exploit that fact that $ClO_2$ is heavier than many air molecules, a particular configuration of a modular/portable decontamination system was designed. The test house from Example 6 was used. All ducts and 34 of the register vents around the house were sealed. An activating unit was placed in each of six rooms on the upper floor. Each unit had its own variable speed blower, activating cup, and three-conduit system for reagents, water and neutralizing solution as provided on the main unit. Unsealed vents were fitted with a connection that covered the vent but had anti-static tubing going back to the activating unit. If there was more than one register vent in a room, a second connection and tubing was installed and run back to the blower on the activator's intake side. This resulted in providing a mini loop circulation per room while remaining open to the main trunk of the HVAC. The main decontamination system unit was placed in the basement attached to the main trunk of the HVAC system making a closed loop which included the entire house. One MB-10 tablet was in each activating unit, while three tablets were used in the main unit, for a total of 9 tablets. The blowers were turned on low for $ClO_2$ activation. Two biological indicators were placed in the main HVAC trunk area and the cycle lasted 4 hours. At the end of the cycle the valve to the activating cups was closed and the neutralizing area was opened. Blowers were adjusted to high speed and $ClO_2$ gas was entirely evacuated in 20 minutes.

The biological indicators indicated that sterilization of the HVAC system was successfully effectuated.

It is expressly contemplated that each of the various aspects, embodiments, and features thereof described herein may be freely combined with any or all other aspects, embodiments, and features. The resulting aspects and embodiments (e.g., products and methods) are within the scope of the invention. It should be understood that headings herein are provided for purposes of convenience and do not imply any limitation on content included below such heading or the use of such content in combination with content included below other headings.

All articles, books, patent applications, patents, other publications mentioned in this application are incorporated herein by reference. In the event of a conflict between the specification and any of the incorporated references the specification (including any amendments thereto) shall control. Unless otherwise indicated, art-accepted meanings of terms and abbreviations are used herein.

In the claims articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim. For example, any claim that is dependent on another claim may be modified to include one or more elements, limitations, clauses, or descriptive terms, found in any other claim that is dependent on the same base claim. Furthermore, where the claims recite a product, it is to be understood that methods of using the product according to any of the methods disclosed herein, and methods of making the product, are included within the scope of the invention, unless otherwise indicated or unless it would be evident to one of ordinary skill in the art that a contradiction or inconsistency would arise.

Where elements are presented as lists, it is to be understood that each subgroup of the elements is also disclosed, and any element(s) may be removed from the group. The invention provides all such embodiments.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments of the invention, to the tenth of the unit of the lower limit of the range, unless the context clearly dictates otherwise. Any one or more embodiment(s), element(s), feature(s), aspect(s), component(s) etc., of the present invention may be explicitly excluded from any one or more of the claims.

Those skilled in the art will recognize, or be able to ascertain using no more than routine experimentation, many equivalents to the specific embodiments of the invention described and exemplified herein. The scope of the present invention is not intended to be limited to the above Description and Examples, but rather is as set forth in the appended claims.

What is claimed:

1. A decontamination system comprising:
   a chlorine dioxide ($ClO_2$) fumigant activating area having an inlet and an outlet,
   an air blower in fluid communication with the $ClO_2$ fumigant activating area and operable to blow air through said fumigant activating area between said inlet and said outlet; and,
   an open activation cup configured to selectively receive reagents and water for selective in situ generation of $ClO_2$ fumigant, wherein the cup is located in the fumigant activation area so as to be exposed to the air flowing through the fumigant activation area, wherein the cup is formed of an outer layer, an inner layer, and a filter layer interposed between the outer and inner layers, and wherein the cup is substantially permeable to gas and substantially impermeable to water and reaction byproducts;
   whereby $ClO_2$ fumigant generated by the reaction of the reagents and water in the cup passes out the outlet of the activation area with the air flow.

2. The decontamination system according to claim 1, wherein said activation cup is molded into an aerodynamically-shaped shell, said shell being open at the top and having an interior and an exterior surface.

3. The decontamination system according to claim 2, wherein the aerodynamic shape of the shell comprises a substantially triangular shape, a teardrop shape, a pear shape, or a saddle shape.

4. The decontamination system according to claim 2, wherein at least one of said exterior surface and said interior surface of the shell comprises a pattern of corrugations effective to create turbulence in the airflow around and through the cup resulting in vibration of the cup and accelerated activation of $ClO_2$ fumigant.

5. The decontamination system according to claim 1, wherein the activation area provides for the selective addition of water, dry reagents, and neutralizing agents to the activation cup.

6. The decontamination system according to claim 5, wherein the activation area comprises a plurality of conduits with valves adapted for the selective controlled metered addition of water, addition of dry reagents, and addition of neutralizing reagents to the activation cup.

7. The decontamination system according to claim 5, wherein said activation area provides for the selective addition of dry reagents and water to the activation cup without removing the activation cup from the activation area.

8. The decontamination system according to claim 5, wherein said activation area provides for the selective addition of dry reagents and water to the activation cup while a decontamination process is in progress.

9. The decontamination system according to claim 1, including:
   a by-pass flow area;
   a valve system operable to selectively bring said air blower into fluid communication with said by pass flow area and to remove fluid communication between said air blower said fumigant activating area;
   whereby, air flow may be caused selectively to by-pass said fumigant activating area.

10. The decontamination system according to claim 9, wherein the by-pass flow area provides for the selective addition of neutralizing reagents to the air flow.

11. The decontamination system according to claim 1 including a neutralizing area operable to receive and neutralize $ClO_2$ fumigant, the neutralizing area having an inlet and an outlet and being in selective fluid communication with an air blower operable to blow air containing $ClO_2$ fumigant through said neutralizing area between said inlet and said outlet, wherein the neutralizing area comprises at least one of the following:
   (a) a first treatment station comprising ultraviolet light (UV);
   (b) a second treatment station comprising a reservoir of liquid neutralizing solution;
   (c) a third treatment station comprising a humidification filter, said humidification filter configured to capture, contain and return neutralizing solution while permitting substantially treated air to pass through; and
   (d) a fourth treatment station comprising coated zeolite.

12. The decontamination system according to claim 11, wherein the liquid neutralizing solution comprises sodium thiosulfate and water.

13. The decontamination system according to claim 11, wherein the zeolite is coated with sodium thiosulfate.

14. The decontamination system according to claim 13, wherein said neutralizing area further comprises:
   activated charcoal suitable for removing odiferous molecules from the treated air.

15. The decontamination system according to claim 11, wherein the humidification filter comprises a humidification pad and humidification fins, said humidification fins comprising grooves and being aligned beneath the humidification pad.

16. The decontamination system according to claim 11 including a leak abatement space enclosing said fumigant activating area and said neutralizing area, wherein the leak abatement space comprises:
   (f) an air blower adapted for pulling treated air through an exit port of the neutralizing space and into the leak abatement space;
   (g) a fifth treatment station comprising a housing comprising UV light; and
   (h) a second air blower set to blow air from the leak abatement space through the fifth treatment station back into an inlet of the neutralizing area.

17. The decontamination system according to claim 16, wherein the leak abatement space further comprises:
   a sealed housing; and,
   one or more hoses connecting the leak abatement space to an environment external to the sealed housing, including at least one hose connected to the second air blower to pull potentially contaminated air from the external environment and direct it into the fifth treatment station.

18. The decontamination system according to claim 11, wherein said neutralizing area includes an inlet for receiving air from said air blower and a valve operable to selectively control the flow of air between said air blower and said inlet.

19. The decontamination system according to claim 1, comprising multiple independently housed activating areas and at least one neutralizing area.

20. The decontamination system according to claim 19 adapted to decontaminate an HVAC system and configured as an open-loop system, said HVAC system comprising an HVAC unit and HVAC duct work, wherein an activating area housing is in fluid communication with a neutralizing area housing via the HVAC duct work.

21. The decontamination system according to claim 20, wherein multiple independently housed activating areas are located relative to the HVAC unit such that gravity aids in distribution of $ClO_2$ fumigant through the duct work.

22. The decontamination system according to claim 1, comprising a neutralizing area operable to receive and neutralize $ClO_2$ fumigant, wherein the activating area and neutralizing area are housed together in one sealed housing.

23. The decontamination system according to claim 22, wherein said sealed housing comprising a $ClO_2$ fumigant outlet port and a $ClO_2$ waste air inlet port, the decontamination system further comprising: a decontamination chamber separate from said sealed housing, said decontamination chamber configured to hold a product to be decontaminated and comprising an inlet port connected to the $ClO_2$ fumigant outlet port and an outlet port connected to the $ClO_2$ waste air inlet port to form a closed loop decontamination system.

24. The decontamination system according to claim 23, wherein the decontamination chamber comprises an inner containment structure and an outer skin and having an air space between the inner containment structure and outer skin, said inner structure and outer skin fabricated from a fire and blast retardant material and having an anti-static coating on surfaces operationally contacted with $ClO_2$ fumigant or $ClO_2$ waste air.

25. The decontamination system according to claim 24, wherein the decontamination chamber further comprises at least one air blower positioned in the air space.

26. The decontamination system according to claim 23, wherein the decontamination system is portable.

27. The decontamination system according to claim 23, comprising a $ClO_2$ fumigant concentration monitoring device, said device comprising at least one $ClO_2$ sensor in communication with an interior space of the decontamination chamber.

28. The decontamination system according to claim 27, comprising a $ClO_2$ fumigant leakage monitoring device comprising a $ClO_2$ sensor located in a space external to said decontamination chamber.

* * * * *